US005178663A

United States Patent [19]

Harada et al.

[11] Patent Number: 5,178,663

[45] Date of Patent: Jan. 12, 1993

[54] 3-ALKOXYALKANOIC ACID DERIVATIVE, PROCESS FOR PREPARING THE SAME AND HERBICIDE USING THE SAME

[75] Inventors: Katsumasa Harada; Takaaki Abe; Yuji Akiyoshi; Hiroshi Shiraishi; Kaoru Yamamoto, all of Ube, Japan

[73] Assignee: UBE Industries, Ltd., Yamaguchi, Japan

[21] Appl. No.: 779,238

[22] Filed: Oct. 18, 1991

[30] Foreign Application Priority Data

Oct. 19, 1990 [JP] Japan .................................. 2-279328

Apr. 23, 1991 [JP] Japan .................................. 3-189613

[51] Int. Cl.⁵ ..................... A01N 43/54; C07D 239/60

[52] U.S. Cl. .................................... 504/242; 544/301; 544/302; 544/303; 544/304; 544/306; 544/309; 544/312; 544/313; 544/314; 544/315; 544/316; 544/318; 504/243

[58] Field of Search ................................ 544/301-304, 544/306, 309, 312-316, 318; 71/92

[56] References Cited

U.S. PATENT DOCUMENTS

| | | | |
|---|---|---|---|
| 4,468,340 | 11/1990 | Kaku et al. | 544/302 |
| 4,889,552 | 12/1989 | Wada et al. | 544/302 |
| 4,900,352 | 2/1990 | Wada et al. | 544/302 |
| 4,923,501 | 5/1990 | Saito et al. | 544/302 |
| 4,932,999 | 6/1990 | Saito et al. | 544/302 |
| 4,946,495 | 8/1990 | Wada et al. | 544/302 |
| 5,015,285 | 5/1991 | Rheinheimer et al. | 544/302 |
| 5,057,143 | 10/1991 | Rheinheimer et al. | 544/302 |
| 5,085,686 | 2/1992 | Vogelbacher et al. | 544/302 |

FOREIGN PATENT DOCUMENTS

| | | |
|---|---|---|
| 347811 | 12/1989 | European Pat. Off. . |
| 409368 | 1/1991 | European Pat. Off. . |
| 0409369A2 | 1/1991 | European Pat. Off. . |
| 3-135963 | 6/1991 | Japan . |

*Primary Examiner*—Cecilia Tsang

*Attorney, Agent, or Firm*—Finnegan, Henderson, Farabow, Garrett and Dunner

[57] ABSTRACT

Disclosed is a 3-alkoxyalkanoic acid compound represented by the following formula (I):

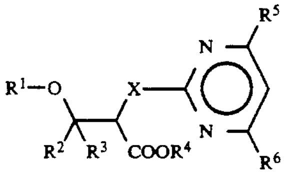

(I)

wherein $R^1$ represents a lower alkyl group, a lower alkenyl group, a lower alkynyl group, a cycloalkyl group, a halo-lower alkyl group or a cyano-lower alkyl group; $R^2$ represents hydrogen atom or a lower alkyl group; $R^3$ represents a lower alkyl group or a cycloalkyl group; or $R^2$ and $R^3$ are mutually bonded to represent a cycloalkyl group; $R^4$ represents hydrogen atom, a lower alkyl group or a lower alkynyl group; $R^5$ represents a lower alkoxy group, a lower alkyl group, a halogen atom or a halo-lower alkyl group; $R^6$ represents a lower alkoxy group or a lower alkyl group; and X represents oxygen atom or sulfur atom, or an alkali addition salt thereof, processes for preparing the same and herbicides containing the same as an active ingredient(s).

10 Claims, No Drawings

3-ALKOXYALKANOIC ACID DERIVATIVE, PROCESS FOR PREPARING THE SAME AND HERBICIDE USING THE SAME

BACKGROUND OF THE INVENTION

This invention relates to a herbicide containing a novel 3-alkoxyalkanoic acid derivative as an active ingredient.

Many herbicides have heretofore been developed for promoting labor-saving of farm practices and increase in productivity of crops. Conventional herbicides are, however, not sufficient in herbicidal effect, and also not sufficiently satisfactory in the point of safety to creatures. Thus, in order to solve these problems, development of a novel herbicide has been demanded.

As a compound similar to the novel 3-alkoxyalkanoic acid derivative of the present invention, there has been known, for example, compounds disclosed in Japanese Provisional Patent Publication No. 85262/1990, and it has been also known that these compounds have herbicidal activities.

However, in the above patent publication, there are descriptions about 3-hydroxyalkanoic acid derivatives and 4-hydroxyalkanoic acid derivatives, but there is no description about a 3-alkoxyalkanoic acid derivative.

Thus, it has been not known that a 3-alkoxyalkanoic acid derivative has herbicidal effects, and further has more excellent herbicidal effect than the compounds disclosed in the above patent publication.

SUMMARY OF THE INVENTION

An object of the present invention is to provide a novel 3-alkoxyalkanoic acid derivative or an alkali addition salt thereof, a process for preparing the same and a herbicide which contains said compound as an active ingredient.

The present inventors have studied intensively in order to solve the above problems, and consequently found that a novel 3-alkoxyalkanoic acid derivative shows more excellent herbicidal effect than the compounds disclosed in Japanese Provisional Patent Publication No. 85262/1990 (a 3-hydroxyalkanoic acid derivative and a 4-hydroxyalkanoic acid derivative), to accomplish the present invention.

The present invention is described below.

That is, the first invention is concerned to a 3-alkoxyalkanoic acid derivative represented by the following formula (I):

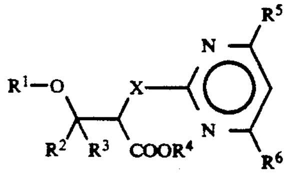
(I)

wherein $R^1$ represents a lower alkyl group, a lower alkenyl group, a lower alkynyl group, a cycloalkyl group, a halo-lower alkyl group or a cyano-lower alkyl group; $R^2$ represents hydrogen atom or a lower alkyl group; $R^3$ represents a lower alkyl group or a cycloalkyl group; or $R^2$ and $R^3$ are mutually bonded to represent a cycloalkyl group; $R^4$ represents hydrogen atom, a lower alkyl group or a lower alkynyl group; $R^5$ represents a lower alkoxy group, a lower alkyl group, a halogen atom or a halo-lower alkyl group; $R^6$ represents a lower alkoxy group or a lower alkyl group; and X represents oxygen atom or sulfur atom, or an alkali addition salt thereof.

The second invention is concerned to a process for preparing the 3-alkoxyalkanoic acid derivative represented by the above formula (I), which comprises reacting a compound represented by the following formula (II):

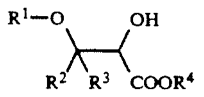
(II)

wherein $R^1$, $R^2$, $R^3$ and $R^4$ each have the same meanings as defined above, with a compound represented by the following formula (III):

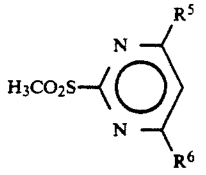
(III)

wherein $R^5$ and $R^6$ each have the same meanings as defined above.

The third invention is concerned to a process for preparing the 3-alkoxyalkanoic acid derivative represented by the above formula (I), which comprises reacting a compound represented by the following formula (IV):

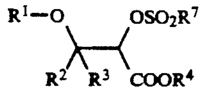
(IV)

wherein $R^1$, $R^2$, $R^3$ and $R^4$ each have the same meanings as defined above; and $R^7$ represents a lower alkyl group, a substituted phenyl group or a halo-lower alkyl group, with a compound represented by the following formula (V):

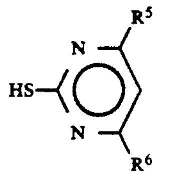
(V)

wherein $R^5$ and $R^6$ each have the same meanings as defined above.

The fourth invention is concerned to a process for preparing the 3-alkoxyalkanoic acid derivative represented by the above formula (I), which comprises hydrolyzing a compound represented by the following formula (VI):

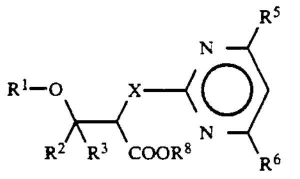

(VI)

wherein $R^1$, $R^2$, $R^3$, $R^5$, $R^6$ and X each have the same meanings as defined above; and $R^8$ represents a lower alkyl group or a lower alkynyl group, The fifth invention is concerned to a herbicide comprising the 3-alkoxyalkanoic acid derivative represented by the above formula (I) or an alkali addition salt thereof as an active ingredient.

DESCRIPTION OF THE PREFERRED EMBODIMENTS

In the following, the present invention is explained in detail.

In the novel 3-alkoxyalkanoic acid derivative (I) which is the desired compound of the present invention and the compounds (II) to (VI) which are starting materials thereof, $R^1$, $R^2$, $R^3$, $R^4$, $R^5$, $R^6$, $R^7$, $R^8$ and X are as described below.

As $R^1$, there may be mentioned a lower alkyl group, a lower alkenyl group, a lower alkynyl group, a cycloalkyl group, a halo-lower alkyl group and a cyano-lower alkyl group, preferably a lower alkyl group (e.g. a straight or branched alkyl group having 1 to 6 carbon atoms which may be substituted by a cycloalkyl group having 3 to 8 carbon atoms), a lower alkenyl group (e.g. a straight or branched alkenyl group having 2 to 6 carbon atoms), a lower alkynyl group (e.g. a straight or branched alkynyl group having 2 to 6 carbon atoms), a cycloalkyl group (e.g. a cycloalkyl group having 3 to 8 carbon atoms), a halo-lower alkyl group (e.g. a straight or branched haloalkyl group having 2 to 6 carbon atoms) and a cyano-lower alkyl group (e.g. a straight or branched cyanoalkyl group having 2 to 6 carbon atoms). The lower alkyl group is more preferably an alkyl group having 1 to 4 carbon atoms (e.g. methyl group, ethyl group, n-propyl group, i-propyl group, n-butyl group, i-butyl group, sec-butyl group and t-butyl group) or a straight or branched alkyl group having 1 to 3 carbon atoms which may be substituted by a cycloalkyl group having 3 to 5 carbon atoms (e.g. cyclopropylmethyl group and cyclobutylmethyl group), the lower alkenyl group is more preferably a straight or branched alkenyl group having 2 to 5 carbon atoms (e.g. propenyl group), the lower alkynyl group is more preferably a straight or branched alkynyl group having 2 to 5 carbon atoms (e.g. propynyl group), the cycloalkyl group is more preferably a cycloalkyl group having 3 to 6 carbon atoms (e.g. cyclopentyl group), the halo-lower alkyl group is more preferably a straight or branched halo-lower alkyl group having 2 to 4 carbon atoms (e.g. 2-chloroethyl group and 2-trifluoroethyl group) and the cyano-lower alkyl group is more preferably a straight or branched cyanoalkyl group having 2 to 4 carbon atoms (e.g. 2-cyanoethyl group).

As $R^2$, there may be mentioned hydrogen atom and a lower alkyl group, and the lower alkyl group is preferably a straight or branched alkyl group having 1 to 5 carbon atoms (e.g. those having 1 to 5 carbon atoms as described above).

As $R^3$, there may be mentioned a lower alkyl group and a cycloalkyl group, preferably a lower alkyl group (e.g. a straight or branched alkyl group having 1 to 6 carbon atoms), and the lower alkyl group is preferably a straight or branched alkyl group having 1 to 5 carbon atoms (e.g. those having 1 to 5 carbon atoms as described above).

Or else, $R^2$ and $R^3$ may be mutually bonded to form a cycloalkyl group (e.g. a cycloalkyl group having 3 to 8 carbon atoms), and the cycloalkyl group is more preferably a cycloalkyl group having 3 to 6 carbon atoms (e.g. cyclopentyl group and cyclohexyl group).

As $R^4$, there may be mentioned hydrogen atom, a lower alkyl group and a lower alkynyl group. The lower alkyl group is preferably a straight or branched alkyl group having 1 to 5 carbon atoms (e.g. those having 1 to 5 carbon atoms as described above), and the lower alkynyl group is more preferably a straight or branched alkynyl group having 2 to 5 carbon atoms (e.g. propynyl group).

As $R^5$, there may be mentioned a lower alkoxy group, a lower alkyl group, a halogen atom and a halo-lower alkyl group.

The lower alkoxy group is preferably a straight or branched alkoxy group having 1 to 5 carbon atoms (e.g. methoxy group, ethoxy group, isopropyloxy group and propyloxy group), more preferably methoxy group. The lower alkyl group is preferably a straight or branched alkyl group having 1 to 5 carbon atoms (e.g. those having 1 to 5 carbon atoms as described above), more preferably methyl group. The halogen atom (e.g. fluorine atom, chlorine atom, bromine atom and iodine atom) is preferably chlorine atom. The halo-lower alkyl group is preferably a straight or branched alkyl group having 1 to 5 carbon atoms (e.g. trifluoromethyl group), more preferably trifluoromethyl group.

As $R^6$, there may be mentioned a lower alkoxy group and a lower alkyl group. The lower alkoxy group is preferably a straight or branched alkoxy group having 1 to 5 carbon atoms (e.g. those having 1 to 5 carbon atoms as described above), more preferably methoxy group. The lower alkyl group is preferably a straight or branched alkyl group having 1 to 5 carbon atoms (e.g. those having 1 to 5 carbon atoms as described above), more preferably methyl group.

As $R^7$, there may be mentioned a lower alkyl group, a substituted phenyl group and a halo-lower alkyl group (e.g. those as described above).

As $R^8$, there may be mentioned a lower alkyl group (e.g. those having 1 to 5 carbon atoms as described above) and a lower alkynyl group (e.g. those having 2 to 5 carbon atoms as described above).

As X, there may be mentioned oxygen atom and sulfur atom.

The desired compound (I) can form an alkali addition salt easily with —COO− by using an alkali metal (e.g. sodium or potassium) or an organic amine (e.g. monosubstituted or disubstituted alkylamine).

The novel 3-alkoxyalkanoic acid derivative (I) which is a desired compound may include an optical isomer based on an asymmetric carbon atom.

The compound (I) can be prepared by, for example, Preparation method 1 to Preparation method 3 shown below.

(Preparation method 1)

-continued

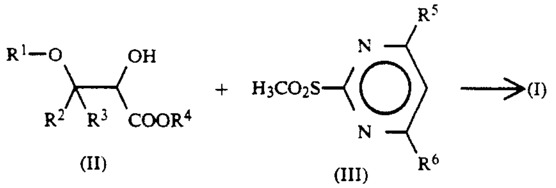

(II) (III)

In general, the compound (I) is preferably prepared by reacting the starting compound (II) with the starting compound (III) in a solvent in the presence of a base, but it can be also obtained by reacting the starting compounds (II) and (III) by melting under heat in the absence of a solvent.

The compound (II) can be prepared easily by, for example, reacting epoxyalkanoates prepared according to the method described in "Tetrahedron Letter", No. 36, p. 3761 (1972) or "Org. Syn.", IV, p. 459 in an alcohol in the presence of an acid catalyst (sulfuric acid or paratoluenesulfonic acid) as shown below.

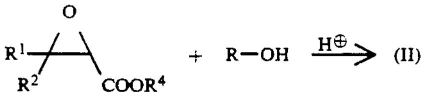

wherein $R^1$, $R^2$ and $R^4$ each have the same meanings as defined above; and R represents an alkyl group.

As the compound (II), there may be mentioned, for example, the respective compounds (referred to as Compounds $(II)_1$ to $(II)_{176}$) comprising the respective kinds of substituted groups corresponding to Compounds No. 1 to No. 172 shown in Table 1, preferably Compounds Nos. 1, 2, 6, 8, 10, 12, 14, 16, 18, 20, 22, 23, 25, 27, 29, 31, 32, 36, 38, 40, 42, 44, 46, 48, 50, 51, 55, 57, 59, 61, 63, 65, 67, 69, 71, 73, 74, 76, 78, 79, 80, 81, 84, 85, 86, 89, 91, 93, 95, 97, 98, 100, 101, 103, 105, 106, 110, 114, 116, 118, 119, 123, 124, 125, 127, 128, 129, 131, 133, 135, 137, 139, 141, 143, 144, 146, 152, 154, 159, 162, 164, 166, 168, 170 and 174 (for example, the compound (II) corresponding to Compound No. 1 is referred to as Compound $(II)_1$, and this Compound $(II)_1$ means a compound wherein $R^1$ is $CH_3$, $R^2$ is H, $R^3$ is $CH_3$ and $R^4$ is $CH_3$ in the compound (II)).

The compound (III) can be prepared easily according to, for example, the method disclosed in Japanese Provisional Patent Publication No. 23870/1988.

As the compound (III), there may be mentioned, for example, the respective compounds (referred to as Compounds $(III)_1$ to $(III)_{176}$) comprising the respective kinds of substituted groups corresponding to Compounds No. 1 to No. 176 shown in Table 1, preferably Compounds Nos. 1, 2, 6, 8, 10, 12, 14, 16, 18, 20, 22, 23, 25, 27, 29, 31, 32, 36, 38, 40, 42, 44, 46, 48, 50, 51, 55, 57, 59, 61, 63, 65, 67, 69, 71, 73, 74, 76, 78, 79, 80, 81, 84, 85, 86, 89, 91, 93, 95, 97, 98, 100, 101, 103, 105, 106, 110, 114, 116, 118, 119, 123, 124, 125, 127, 128, 129, 131, 133, 135, 137, 139, 141, 143, 144, 146, 152, 154, 159, 162, 164, 166, 168, 170 and 174 (for example, the compound (III) corresponding to Compound No. 1 is referred to as Compound $(III)_1$, and this Compound $(III)_1$ means a compound wherein $R^5$ and $R^6$ are each $OCH_3$ in the compound (III)).

The solvent is not particularly limited so long as it does not participate in the present reaction directly, and may include, for example, chlorinated or unchlorinated aromatic or aliphatic hydrocarbons such as benzene, toluene, xylene, methylnaphthalene, chlorobenzene, dichlorobenzene, methylene chloride, chloroform and dichloroethane; ethers such as diethyl ether, tetrahydrofuran and dioxane; ketones such as acetone and methyl ethyl ketone or hydrates thereof; amides such as N,N-dimethylformamide and N,N-dimethylacetamide; 1,3-dimethyl-2-imidazolidinone; dimethyl sulfoxide; and a mixture of the above solvents.

As the base, there may be mentioned, for example, organic bases such as triethylamine, pyridine and N,N-diethylaniline; and inorganic bases such as sodium amide, sodium hydroxide, potassium hydroxide, potassium carbonate, sodium carbonate and sodium hydride.

The reaction for preparing the compound (I) can be carried out at a reaction concentration of 5 to 100%.

In the preparation method, the ratio of the starting compound (II) to the starting compound (III) to be used is 0.5 to 2 mole, preferably 1 to 1.5 mole of the starting compound (III) per mole of the starting compound (II).

The reaction temperature is not particularly limited so long as it is the boiling point of a solvent used or lower. However, the reaction can be carried out generally at room temperature or higher, and it is preferred to carry out the reaction by heating to shorten the reaction time.

The reaction time varies depending on the above concentration and temperature, but may be generally 1 to 12 hours.

As the compound (I), there may be mentioned, for example, the respective compounds (referred to as Compounds 1 to 176) comprising the respective kinds of substituted groups corresponding to Compounds No. 1 to No. 176 shown in Table 1, preferably Compounds Nos. 1, 2, 6, 8, 10, 12, 14, 16, 18, 20, 22, 23, 25, 27, 29, 31, 32, 36, 38, 40, 42, 44, 46, 48, 50, 51, 55, 57, 59, 61, 63, 65, 67, 69, 71, 73, 74, 76, 78, 79, 80, 81, 84, 85, 86, 89, 91, 93, 95, 97, 98, 100, 101, 103, 105, 106, 110, 114, 116, 118, 119, 123, 124, 125, 127, 128, 129, 131, 133, 135, 137, 139, 141, 143, 144, 146, 152, 154, 159, 162, 164, 166, 168, 170 and 174 (for example, the compound (I) corresponding to Compound No. 1 is referred to as Compound 1, and this Compound 1 means a compound wherein $R^1$ is $CH_3$, $R^2$ is H, $R^3$ is $CH_3$, $R^4$ is $CH_3$, $R^5$ and $R^6$ are each $OCH_3$ and X is O in the compound (I)).

(Preparation method 2)

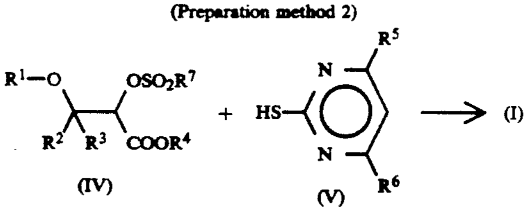

(IV) (V)

wherein $R^1$, $R^2$, $R^3$, $R^4$, $R^5$, $R^6$ and $R^7$ each have the same meanings as defined above.

The compound (I) can be obtained by carrying out the reaction in the same manner as in Preparation method 1 except for using the starting compound (IV) in place of the starting compound (II) and using the starting compound (V) in place of the starting compound (III).

As the compound (IV), there may be mentioned, for example, the respective compounds (referred to as Compounds $(IV)_1$ to $(IV)_{176}$) comprising the respective kinds of substituted groups corresponding to Compounds No. 1 to No. 176 shown in Table 1, preferably Compounds Nos. 4, 34, 35, 53, 54, 88, 108, 109, 113, 121, 122, 156, 157, 158, 161, 169, 172, 173 and 176 (for example, the compound (IV) corresponding to Compound No. 4 is referred to as Compound $(IV)_4$, and this Compound $(IV)_4$ means a compound wherein $R^1$ is $CH_3$, $R^2$ is H, $R^3$ is $CH_3$, $R^4$ is $C_2H_5$ and $R^7$ is a substituted phenyl group in the compound (IV)).

As the compound (V), there may be mentioned, for example, the respective compounds (referred to as Compounds $(V)_1$ to $(V)_{176}$) comprising the respective kinds of substituted groups corresponding to Compounds No. 1 to No. 176 shown in Table 1, preferably Compounds Nos. 4, 34, 35, 53, 54, 88, 108, 109, 113, 121, 122, 156, 157, 158, 161, 169, 172, 173 and 176 (for example, the compound (V) corresponding to Compound No. 4 is referred to as Compound $(V)_4$, and this Compound $(V)_4$ means a compound wherein $R^5$ and $R^6$ are each $OCH_3$ in the compound (V)).

The starting compound (V) to be used in the present invention can be prepared easily by, for example, adding sodium hydrosulfide to a corresponding 2-methylsulfonylpyrimidine derivative and stirring the mixture in water or an alcohol under heating.

The reaction for preparing the compound (I) can be carried out at a reaction concentration of 5 to 80%.

In the preparation method, the ratio of the starting compound (IV) to the starting compound (V) to be used is 0.5 to 2 mole, preferably 1 to 1.5 mole of the starting compound (V) per mole of the starting compound (IV).

As the solvent and base, those described in Preparation method 1 can be used.

The reaction temperature is not particularly limited so long as it is the boiling point of a solvent used or lower. However, the reaction can be carried out generally at room temperature or higher, and the temperature range is preferably 10° to 80° C., more preferably 20° to 50° C.

The reaction time varies depending on the above concentration and temperature, but may be generally 1 to 12 hours.

(Preparation method 3)

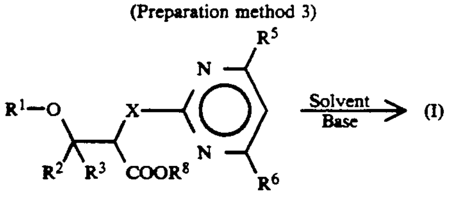

(VI)

wherein $R^1$, $R^2$, $R^3$, $R^5$, $R^6$, $R^8$ and X each have the same meanings as defined above.

The compound (1) can be generally prepared by reacting the starting compound (VI) in a solvent in the presence of a base.

As the compound (VI), there may be mentioned, for example, the respective compounds (referred to as Compounds 1 to 176) comprising the respective kinds of substituted groups corresponding to Compounds No. 1 to No. 176 shown in Table 1, preferably Compounds Nos. 3, 7, 9, 11, 13, 15, 17, 19, 21, 24, 26, 28, 30, 33, 37, 39, 41, 43, 45, 47, 49, 52, 56, 58, 60, 62, 64, 66, 68, 70, 72, 75, 77, 82, 87, 90, 92, 94, 96, 99, 102, 104, 107, 111, 115, 117, 120, 126, 130, 132, 134, 136, 138, 140, 142, 145, 147, 153, 155, 160, 163, 165, 167, 171 and 175 (for example, the compound (VI) corresponding to Compound No. 3 is referred to as Compound $(VI)_3$, and this Compound $(VI)_3$ means a compound wherein $R^1$ is $CH_3$, $R^2$ is H, $R^3$ is $CH_3$, $R^4$ is $C_2H_5$, $R^5$ and $R^6$ are each $OCH_3$ and X is O in the compound (VI)).

As the solvent, there may be mentioned alcohols such as methanol and ethanol; ethers such as 1,4-dioxane and tetrahydrofuran; ketones such as acetone and methyl ethyl ketone; water; and a mixture of the above solvents.

As the base, there may be mentioned sodium hydroxide and potassium hydroxide.

The reaction temperature is not particularly limited so long as it is the boiling point of a solvent used or lower, but the reaction can be carried out generally at room temperature or higher and it is preferred to carry out the reaction in the range of 10° to 80° C., preferably 20° to 50° C.

The reaction time varies depending on the following concentration and temperature, but may be generally 1 to 12 hours.

The reaction is generally carried out under the concentration of 5 to 60%.

An alkali addition salt of the compound (I) can be obtained by reacting the compound (I) with a monoequivalent or diequivalent alkali metal or an organic amine in an organic solvent (e.g. an ether or an alcohol) or water at room temperature for 1 to 24 hours.

The herbicide containing the compound (I) or an alkali addition salt thereof as an active ingredient has high selectivity and also shows excellent herbicidal effect.

That is, the herbicide of the present invention shows excellent herbicidal effect on annual weeds and perennial weeds grown in paddy fields and upland fields, and its herbicidal effect is particularly remarkable in annual grass weeds (e.g. crabgrass (manna-grass), barnyardgrass and foxtail (green panicum)), annual broad-leaved weeds (e.g. morning glory, common lambsquarter (white goosefoot), livid amaranthus and velvetleaf) and perennial weeds (e.g. Johnson grass).

The herbicide of the present invention shows excellent herbicidal effect on the weeds described above, but does not give chemical damage on field crops (e.g. cotton) at a concentration for such a treatment.

The herbicide of the present invention contains the compound (I) or at least one alkali addition salt thereof as an active ingredient(s).

The compound (I) can be used singly, but may be preferably used by mixing with a carrier, a surfactant, a dispersant and an auxiliary (for example, prepared as a composition such as a dust, an emulsion, a fine granule, a granule, a wettable powder, an oily suspension and an aerosol) according to a conventional method.

As the carrier, there may be mentioned, for example, a solid carrier such as talc, mica, bentonite, clay, kaolin, diatomaceous earth, white carbon, vermiculite, dolomite, zeolite, slaked lime, siliceous sand, silicic anhydride, ammonium sulfate, urea, wood powder, starch and cellulose; a liquid carrier such as hydrocarbons (kerosine and mineral oil), aromatic hydrocarbons (benzene, toluene and xylene), chlorinated hydrocarbons (chloroform and carbon tetrachloride), ethers (dioxane and tetrahydrofuran), ketones (acetone, cyclohexanone and isophorone), esters (ethyl acetate, ethylene glycol acetate and dibutyl maleate), alcohols (methanol, n-hexanol and ethylene glycol), polar solvents (dimethylformamide and dimethylsulfoxide) and water; and a gas carrier such as air, nitrogen, carbonic acid gas and freon (in the case of a gas carrier, mixed spray can be carried out).

As the surfactant which can be used for improving attachment of the present herbicide to and absorption thereof in plants, and improving characteristics such as dispersion, emulsification and spreading of the herbicide, there may be mentioned nonionic, anionic, cationic or amphoteric surfactants (e.g. alcohol sulfates, alkylsulfonates, lignin sulfonates and polyoxyethylene glycol ethers). Further, for improving properties of preparation, carboxymethyl cellulose, polyethylene glycol or gum arabic can be used as an auxiliary.

In preparation of the present herbicide, in addition to the above carrier, surfactant, dispersant and auxiliary, other agricultural chemicals (a fungicide and an insecticide), a fertilizer and a soil conditioner can be used singly or in a suitable combination, respectively, depending on the respective purposes.

When the compound (I) of the present invention is made into preparations, the concentration of the active ingredient is generally 1 to 50% by weight in an emulsion, generally 0.3 to 25% by weight in a dust, generally 1 to 90% by weight in a wettable powder, generally 0.5 to 5% by weight in a granule, generally 0.5 to 5% by weight in an oily dispersion, and generally 0.1 to 5% by weight in an aerosol.

These preparations can be provided for various uses by diluting them to have a suitable concentration and spraying them to stems and/or leaves of plants, soil and paddy field surface, or by applying them directly thereto, depending on the respective purposes.

EXAMPLES

The present invention is described in detail by referring to Examples, but the scope of the present invention is not limited by these Examples.

Example 1

(1) Synthesis of Ethyl 2-(4,6-Dimethoxypyrimidin-2-yl)oxy-3-ethoxy-3-methylbutanoate (Compound 50)

The compound (I) of the present invention was synthesized according to the method described in (Preparation method 1).

That is, to ethanol (40 ml) was added ethyl 2,3-epoxy-3-methylbutanoate (14.4 g, 0.1 mol) and then sulfuric acid (0.5 ml) was added as a catalyst, and the mixture was stirred at 30° C. for 2 hours.

Subsequently, excessive ethanol was removed under reduced pressure to obtain ethyl 3-ethoxy-2-hydroxy-3-methylbutanoate. After the product obtained and 4,6-dimethoxy-2-methylsulfonylpyrimidine (21.8 g, 0.1 mol) were added to N,N-dimethylformamide (150 ml) and further anhydrous potassium carbonate (16.6 g, 0.12 mol) was added, the mixture was stirred at 60 .C for 3 hours. The resulting reaction mixture was added to water and extracted with ethyl acetate. The ethyl acetate layer was washed with a saturated saline solution and dried over sodium sulfate, and ethyl acetate was removed under reduced pressure. The residue obtained was isolated by column chromatography (Wako gel C-200 (trade name, produced by Wako Junyaku K.K.), eluted by toluene:ethyl acetate =4:1) to obtain 26.5 g (yield: 81%) of the title compound as a white powder.

(2) Synthesis of 2-(4,6-Dimethoxypyrimidin-2-yl)oxy-3-ethoxy-3-methylbutanoic Acid (Compound 52)

The title compound (I) was synthesized according to the method described in (Preparation method 1).

That is, to Compound 50 (32.8 g, 0.1 mol) prepared in the above (1) dissolved in ethanol (100 ml) was added 5N sodium hydroxide (40 ml), and the mixture was stirred for one hour. Subsequently, ethanol was removed under reduced pressure, 5N hydrochloric acid (50 ml) was added to the residue obtained, and the residue was extracted with chloroform. The chloroform layer was washed with water and dried, and then chloroform was removed under reduced pressure to obtain 25.5 g (yield: 85.0%) of the title compound as white crystals.

(3) Synthesis of Sodium 2-(4,6-Dimethoxypyrimidin-2-yl)oxy-3-ethoxy-3-methylbutanoate (Compound 148)

To Compound 52 (30.0 g, 0.1 mol) prepared in the above (2) dissolved in methanol (100 ml) was added sodium methoxide (19.3 g, 28% methanol solution), and the mixture was stirred for 10 minutes. Subsequently, methanol was removed under reduced pressure to obtain 32 g of the title compound as white crystals.

(4) Synthesis of Ethyl 2-(4,6-Dimethoxypyrimidin-2-yl)thio-3-(isopropoxy)-butanoate (Compound 88)

The title compound (I) was synthesized according to the method described in (Preparation method 2).

That is, to ethyl 2,3-epoxybutanoate (13.0 g, 0.1 mol) dissolved in isopropanol (30 ml) was added sulfuric acid (0.5 ml), and the mixture was stirred at 60° C. for 5 hours. Subsequently, excessive isopropanol was removed under reduced pressure to obtain ethyl 3-(isopropoxy)-2-hydroxybutanoate. The product obtained and p-toluenesulfonyl chloride (20.9 g, 0.11 mol) were added to pyridine (50 ml), and the mixture was stirred at room temperature for 5 hours. Subsequently, water was added to the reaction mixture, and the oily product liberated was extracted with toluene. After the toluene layer was washed with water and dried over sodium sulfate, toluene was removed under reduced pressure. The oily product obtained was isolated by silica gel column chromatography (Wako gel C-200 (trade name, produced by Wako Junyaku K.K.), eluted by hexane: ethyl acetate=9:1) to obtain ethyl 3-(isopropoxy)-2-p-toluenesulfonyloxybutanoate (27.5 g).

After this compound, ethyl 3-(isopropoxy)-2-p-toluenesulfonyloxybutanoate (27.5 g, 0.08 mol) and 4,6-dimethoxy-2-mercaptopyrimidine (13.7 g, 0.08 mol) were added to N,N-dimethylformamide (80 ml) and further anhydrous potassium carbonate (11.1 g) was added thereinto, the mixture was stirred at room temperature for 5 hours. Subsequently, water was added to the reaction mixture, the mixture was extracted with ethyl acetate, washed with water and dried, and ethyl acetate was removed under reduced pressure. The residue obtained was isolated by column chromatography (Wako gel C-200 (trade name, produced by Wako Junyaku K.K.), eluted by hexane:ethyl acetate=8:1) to obtain 15.0 g (yield: 54.5%) of the title compound as a colorless oily product.

(5) Synthesis of 2-(4,6-Dimethoxypyrimidin-2-yl)thio-3-methoxy-3-methylbutanoic Acid (Compound 21)

The title compound (I) was synthesized according to the method described in (Preparation method 2).

That is, after 3-methoxy-3-methyl-2-methylsulfonyloxybutanoic acid (22.6 g, 0.1 mol) and 4,6-dimethoxy-2-mercaptopyrimidine (17.3 g, 0.1 mol) were added to N,N-dimethylformamide (200 ml) and further anhydrous potassium carbonate (13.8 g) was added, the mixture was stirred at 50° C. for 2 hours. The resulting reaction mixture was added to a 1N hydrochloric acid aqueous solution (300 ml), and extracted with ethyl acetate. The ethyl acetate layer was washed with a saturated saline solution and dried over magnesium sulfate, and ethyl acetate was removed under reduced pressure. The crystals obtained were washed with n-hexane to obtain 24.1 g (yield: 80%) of the title compound.

(6) Synthesis of Ethyl 2-(4,6-Dimethoxypyrimidin-2-yl)oxy-3-(n-propoxy)-butanoate (Compound 79)

The title compound (I) was synthesized according to the method described in (Preparation method 1).

That is, after ethyl 2,3-epoxy-3-methylbutanoate (14.4 g, 0.1 mol) was added to n-propanol (40 ml) and sulfuric acid (0.5 ml) was added as a catalyst, the mixture was stirred at 30° C. for 4 hours.

Subsequently, excessive n-propanol was removed under reduced pressure to obtain ethyl 2-hydroxy-3-methyl(n-propoxy)butanoate. After the product obtained and 4,6-dimethoxy-2-methylsulfonylpyrimidine (21.8 g, 0.01 mol) were added to acetone (150 ml) and further anhydrous potassium carbonate (16.6 g, 0.12 mol) was added, the mixture was refluxed under heating. The resulting reaction mixture was added to water and extracted with ethyl acetate. The ethyl acetate layer was washed with a saturated saline solution and dried over sodium sulfate, and ethyl acetate was removed under reduced pressure. The residue obtained was isolated by column chromatography (Wako gel C-200 (trade name, produced by Wako Junyaku K.K.), eluted by toluene:ethyl acetate=4:1) to obtain 27.0 g (yield: 80%) of the title compound as a white powder.

(7) Syntheses of Other Compounds (I) in Table 1

In the same manner as in either of the synthetic methods (1) to (6), the title compounds (I) as shown in Table 1 were obtained.

The title compounds (I) obtained as described above are shown in Table 1.

TABLE 1

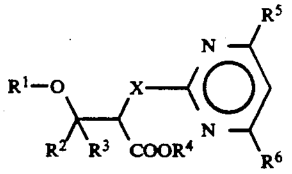

| Compound No. | $R^1$ | $R^2$ | $R^3$ | $R^4$ | $R^5$ | $R^6$ | X | Physical property |
|---|---|---|---|---|---|---|---|---|
| 1 | $CH_3$ | H | $CH_3$ | $CH_3$ | $OCH_3$ | $OCH_3$ | O | m.p. 83~85° C. |
| 2 | " | " | " | $C_2H_5$ | " | " | " | |
| 3 | " | " | " | H | " | " | " | m.p. 127~129° C. |
| 4 | " | " | " | $C_2H_5$ | " | " | S | |
| 5 | " | " | " | H | " | " | " | m.p. 84~86° C. |
| 6 | " | " | " | $C_2H_5$ | $CH_3$ | " | O | |
| 7 | " | " | " | H | " | " | " | |
| 8 | " | " | " | $C_2H_5$ | " | $CH_3$ | " | |
| 9 | $CH_3$ | H | $CH_3$ | H | $CH_3$ | $CH_3$ | O | |
| 10 | " | " | " | $C_2H_5$ | Cl | $OCH_3$ | " | |
| 11 | " | " | " | H | " | " | " | |
| 12 | " | " | " | $C_2H_5$ | $CF_3$ | " | " | |
| 13 | " | " | " | H | " | " | " | |
| 14 | " | " | $C_2H_5$ | $C_2H_5$ | $OCH_3$ | " | " | |
| 15 | " | " | " | H | " | " | " | |
| 16 | " | " | n-$C_3H_7$ | $CH_3$ | " | " | " | $n_D^{24.8}$ 1.4520 |
| 17 | $CH_3$ | H | n-$C_3H_7$ | H | $OCH_3$ | $OCH_3$ | O | m.p. 92~94° C. |
| 18 | " | " | i-$C_3H_7$ | $CH_3$ | " | " | " | $n_D^{28.4}$ 1.4868 |
| 19 | " | " | " | H | " | " | " | |
| 20 | " | $CH_3$ | $CH_3$ | $C_2H_5$ | " | " | " | m.p. 89~91° C. |
| 21 | " | " | " | H | " | " | " | m.p. 143~145° C. |
| 22 | " | " | " | i-$C_3H_7$ | " | " | " | m.p. 73~75° C. |
| 23 | " | " | $C_2H_5$ | $C_2H_5$ | " | " | " | m.p. 70~71° C. |
| 24 | " | " | " | H | " | " | " | m.p. 138~140° C. |
| 25 | $CH_3$ | $CH_3$ | 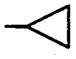 | $C_2H_5$ | $OCH_3$ | $OCH_3$ | O | |
| 26 | " | " | " | H | " | " | " | |
| 27 | " | $C_2H_5$ | $C_2H_5$ | $C_2H_5$ | " | " | " | m.p. 66~67° C. |
| 28 | " | " | " | H | " | " | " | m.p. 163~165° C. |

TABLE 1-continued

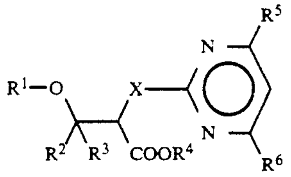

| Compound No. | $R^1$ | $R^2$ | $R^3$ | $R^4$ | $R^5$ | $R^6$ | X | Physical property |
|---|---|---|---|---|---|---|---|---|
| 29 | " | 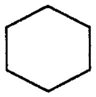 | | $C_2H_5$ | " | " | " | m.p. 109~110° C. |
| 30 | " | " | | H | " | " | " | m.p. 131~133° C. |
| 31 | $C_2H_5$ | H | $CH_3$ | $CH_3$ | " | " | " | Oily product |
| 32 | " | " | " | $C_2H_5$ | " | " | " | m.p. 56~58° C. |
| 33 | $C_2H_5$ | H | $CH_3$ | H | $OCH_3$ | $OCH_3$ | O | m.p. 111~113° C. |
| 34 | " | " | " | $C_2H_5$ | " | " | S | Oily product |
| 35 | " | " | " | H | " | " | " | $n_D^{24.6}$ 1.5238 |
| 36 | " | " | " | $C_2H_5$ | $CH_3$ | " | O | |
| 37 | " | " | " | H | " | " | " | |
| 38 | " | " | " | $C_2H_5$ | " | $CH_3$ | " | |
| 39 | " | " | " | H | " | " | " | |
| 40 | " | " | " | $C_2H_5$ | Cl | $OCH_3$ | O | |
| 41 | $C_2H_5$ | H | $CH_3$ | H | Cl | $OCH_3$ | O | |
| 42 | " | " | " | $C_2H_5$ | $CF_3$ | " | " | |
| 43 | " | " | " | H | " | " | " | |
| 44 | " | " | $C_2H_5$ | $C_2H_5$ | $OCH_3$ | " | " | $n_D^{23.8}$ 1.4704 |
| 45 | " | " | " | H | " | " | " | m.p. 121~123° C. |
| 46 | " | " | n-$C_3H_7$ | $C_2H_5$ | " | " | " | $n_D^{24.8}$ 1.4798 |
| 47 | " | " | " | H | " | " | " | m.p. 123~125° C. |
| 48 | " | " | i-$C_3H_7$ | $C_2H_5$ | " | " | " | $n_D^{26.8}$ 1.4628 |
| 49 | $C_2H_5$ | H | i-$C_3H_7$ | H | $OCH_3$ | $OCH_3$ | O | m.p. 115~117° C. |
| 50 | " | $CH_3$ | $CH_3$ | $C_2H_5$ | " | " | " | m.p. 81~83° C. |
| 51 | " | " | " | t-$C_4H_9$ | " | " | " | |
| 52 | " | " | " | H | " | " | " | m.p. 121~122° C. |
| 53 | " | " | " | $C_2H_5$ | " | " | S | Oily product |
| 54 | " | " | " | H | " | " | " | m.p. 96~98° C. |
| 55 | " | " | " | $C_2H_5$ | $CH_3$ | " | O | $n_D^{23.0}$ 1.4812 |
| 56 | " | " | " | H | " | " | " | m.p. 130~132° C. |
| 57 | $C_2H_5$ | $CH_3$ | $CH_3$ | $C_2H_5$ | $CH_3$ | $CH_3$ | O | |
| 58 | " | " | " | H | " | " | " | |
| 59 | " | " | " | $C_2H_5$ | Cl | $OCH_3$ | " | $n_D^{26.6}$ 1.4858 |
| 60 | " | " | " | H | " | " | " | |
| 61 | " | " | " | $C_2H_5$ | $CF_3$ | " | " | $n_D^{25.0}$ 1.4470 |
| 62 | " | " | " | H | " | " | " | m.p. 73~75° C. |
| 63 | " | " | $C_2H_5$ | $C_2H_5$ | $OCH_3$ | " | " | m.p. 47~85° C. |
| 64 | " | " | " | H | " | " | " | m.p. 83~85° C. |
| 65 | $C_2H_5$ | $CH_3$ | 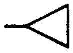 | $C_2H_5$ | $OCH_3$ | $OCH_3$ | O | |
| 66 | " | " | " | H | " | " | " | |
| 67 | " | $C_2H_5$ | $C_2H_5$ | $C_2H_5$ | " | " | " | $n_D^{26.4}$ 1.4815 |
| 68 | " | " | " | H | " | " | " | m.p. 131~133° C. |
| 69 | " | 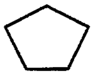 | | $C_2H_5$ | " | " | " | m.p. 82~83° C. |
| 70 | " | " | | H | " | " | " | m.p. 156~158° C. |
| 71 | " | 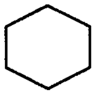 | | $C_2H_5$ | " | " | " | m.p. 89~91° C. |
| 72 | " | " | | H | " | " | " | m.p. 173~175° C. |
| 73 | n-$C_3H_7$ | H | $CH_3$ | $C_2H_5$ | $OCH_3$ | $OCH_3$ | O | $n_D^{26.2}$ 1.4776 |
| 74 | " | " | " | n-$C_3H_7$ | " | " | " | $n_D^{26.6}$ 1.4764 |
| 75 | " | " | " | H | " | " | " | $n_D^{25.6}$ 1.4866 |
| 76 | " | " | n-$C_3H_7$ | $C_2H_5$ | " | " | " | $n_D^{28.5}$ 1.4799 |
| 77 | " | " | " | H | " | " | " | m.p. 129~131° C. |
| 78 | " | " | i-$C_3H_7$ | n-$C_3H_7$ | " | " | " | $n_D^{27.8}$ 1.4718 |
| 79 | " | $CH_3$ | $CH_3$ | $C_2H_5$ | " | " | " | m.p. 51~53° C. |

TABLE 1-continued

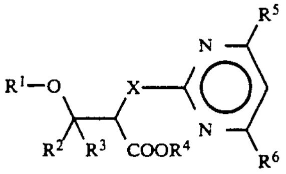

| Compound No. | $R^1$ | $R^2$ | $R^3$ | $R^4$ | $R^5$ | $R^6$ | X | Physical property |
|---|---|---|---|---|---|---|---|---|
| 80 | " | " | " | t-$C_4H_9$ | " | " | " | m.p. 66~68° C. |
| 81 | n-$C_3H_7$ | $CH_3$ | $CH_3$ | $C_2H_5$ | $CF_3$ | $OCH_3$ | O | $n_D^{24.5}$ 1.4480 |
| 82 | " | " | " | H | " | " | " | m.p. 78~80° C. |
| 83 | " | " | " | " | $OCH_3$ | " | " | m.p. 99~101° C. |
| 84 | i-$C_3H_7$ | H | " | $C_2H_5$ | " | " | " | $n_D^{24.0}$ 1.4732 |
| 85 | " | " | " | i-$C_3H_7$ | " | " | " | m.p. 87~89° C. |
| 86 | " | " | " | t-$C_4H_9$ | " | " | " | |
| 87 | " | " | " | H | " | " | " | m.p. 106~108° C. |
| 88 | " | " | " | $C_2H_5$ | " | " | S | $n_D^{27.8}$ 1.5050 |
| 89 | i-$C_3H_7$ | H | $CH_3$ | $C_2H_5$ | $CH_3$ | $OCH_3$ | O | $n_D^{23.3}$ 1.4727 |
| 90 | " | " | " | H | " | " | " | m.p. 117~120° C. |
| 91 | " | " | " | $C_2H_5$ | " | $CH_3$ | " | |
| 92 | " | " | " | H | " | " | " | |
| 93 | " | " | " | $C_2H_5$ | Cl | $OCH_3$ | " | $n_D^{25.0}$ 1.4918 |
| 94 | " | " | " | H | " | " | " | Yellowish oily product |
| 95 | " | " | " | $C_2H_5$ | $CF_3$ | " | " | |
| 96 | " | " | " | H | " | " | " | |
| 97 | i-$C_3H_7$ | H | $C_2H_5$ | $C_2H_5$ | $OCH_3$ | $OCH_3$ | O | $n_D^{25.2}$ 1.4675 |
| 98 | " | " | n-$C_3H_7$ | " | " | " | " | $n_D^{26.8}$ 1.4742 |
| 99 | " | " | " | H | " | " | " | m.p. 129-131° C. |
| 100 | " | " | i-$C_3H_7$ | $C_2H_5$ | " | " | " | $n_D^{26.8}$ 1.4688 |
| 101 | " | " | " | i-$C_3H_7$ | " | " | " | $n_D^{26.8}$ 1.4508 |
| 102 | " | " | " | H | " | " | " | Oily product |
| 103 | " | $CH_3$ | $CH_3$ | $C_2H_5$ | " | " | " | m.p. 64-66° C. |
| 104 | " | " | " | H | " | " | " | Measurement impossible |
| 105 | i-$C_3H_5$ | 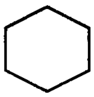 | | $C_2H_5$ | $OCH_3$ | $OCH_3$ | O | $n_D^{27.8}$ 1.4909 |
| 106 | $CH_2{=}CH{-}CH_2{-}$ | H | $CH_3$ | " | " | " | " | $n_D^{25.0}$ 1.4879 |
| 107 | " | " | " | H | " | " | " | m.p. 84~86° C. |
| 108 | " | " | " | $C_2H_5$ | " | " | S | |
| 109 | " | " | " | H | " | " | " | $n_D^{23.6}$ 1.5277 |
| 110 | " | $CH_3$ | " | $C_2H_5$ | " | " | O | m.p. 63~64° C. |
| 111 | " | " | " | H | " | " | " | m.p. 65~67° C. |
| 112 | " | " | " | $C_2H_5$ | " | " | S | |
| 113 | $CH_2{=}CH{-}CH_2{-}$ | $CH_3$ | $CH_3$ | H | $OCH_3$ | $OCH_3$ | S | m.p. 83~84° C. |
| 114 | " | 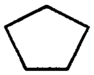 | | $C_2H_5$ | " | " | O | m.p. 53~55° C. |
| 115 | " | " | | H | " | " | " | m.p. 94~95° C. |
| 116 | $HC{\equiv}C{-}CH_2{-}$ | H | $CH_3$ | $C_2H_5$ | " | " | " | $n_D^{27.0}$ 1.4911 |
| 117 | " | " | " | H | " | " | " | $n_D^{24.6}$ 1.5104 |
| 118 | " | $CH_3$ | " | $C_2H_5$ | " | " | " | $n_D^{28.4}$ 1.4960 |
| 119 | " | " | " | $-CH_2C{\equiv}CH$ | " | " | " | $n_D^{28.4}$ 1.5020 |
| 120 | " | " | " | H | " | " | " | m.p. 136~137° C. |
| 121 | $HC{\equiv}C{-}CH_2{-}$ | $CH_3$ | $CH_3$ | $C_2H_5$ | $OCH_3$ | $OCH_3$ | S | |
| 122 | " | " | " | H | " | " | " | m.p. 81~83° C. |
| 123 | n-$C_4H_9$ | H | " | $C_2H_5$ | " | " | O | m.p. 66~68° C. |
| 124 | " | " | " | n-$C_4H_9$ | " | " | " | $n_D^{24.0}$ 1.4750 |
| 125 | " | $CH_3$ | " | $C_2H_5$ | " | " | " | m.p.53~55° C. |
| 126 | " | " | " | H | " | " | " | m.p. 103~104° C. |
| 127 | sec-$C_4H_9$ | H | " | $C_2H_5$ | " | " | " | Measurement impossible |
| 128 | " | " | " | sec-$C_4H_9$ | " | " | " | $n_D^{25.0}$ 1.4738 |
| 129 | sec-$C_4H_9$ | $CH_3$ | $CH_3$ | $C_2H_5$ | $OCH_3$ | $OCH_3$ | O | |
| 130 | " | " | " | H | " | " | " | |
| 131 | i-$C_4H_9$ | H | " | $C_2H_5$ | " | " | " | |
| 132 | " | " | " | H | " | " | " | |
| 133 | " | $CH_3$ | " | $C_2H_5$ | " | " | " | |
| 134 | " | " | " | H | " | " | " | |

TABLE 1-continued
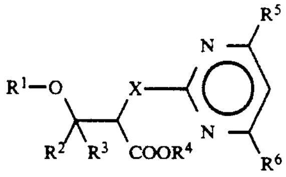
| Compound No. | $R^1$ | $R^2$ | $R^3$ | $R^4$ | $R^5$ | $R^6$ | X | Physical property |
|---|---|---|---|---|---|---|---|---|
| 135 | 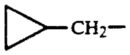 | H | " | $C_2H_5$ | " | " | " | $n_D^{23.6}$ 1.4921 |
| 136 | " | " | " | H | " | " | " | |
| 137 | 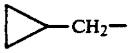 | $CH_3$ | $CH_3$ | $C_2H_5$ | $OCH_3$ | $OCH_3$ | O | m.p. 85~87° C. |
| 138 | " | " | " | H | " | " | " | m.p. 105~106° C. |
| 139 | 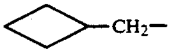 | H | " | $C_2H_5$ | " | " | " | $n_D^{24.8}$ 1.4867 |
| 140 | " | " | " | H | " | " | " | $n_D^{25.0}$ 1.5020 |
| 141 | " | $CH_3$ | " | $C_2H_5$ | " | " | " | m.p. 74~77° C. |
| 142 | " | " | " | H | " | " | " | m.p. 118~119° C. |
| 143 | 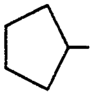 | H | " | $C_2H_5$ | " | " | " | Oily product |
| 144 | $CF_3CH_2$— | " | " | " | " | " | " | $n_D^{26.8}$ 1.4552 |
| 145 | $CF_3CH_2$— | H | $CH_3$ | H | $OCH_3$ | $OCH_3$ | O | |
| 146 | " | $CH_3$ | " | $C_2H_5$ | " | " | " | m.p. 54~56° C. |
| 147 | " | " | " | H | " | " | " | m.p. 128~130° C. |
| 148 | 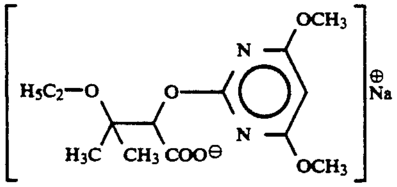 | | | | | | | m.p. 200° C. or higher |
| 149 | 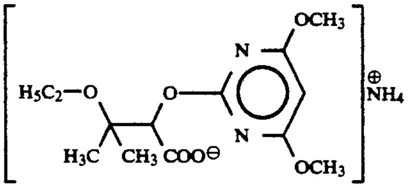 | | | | | | | |
| 150 | 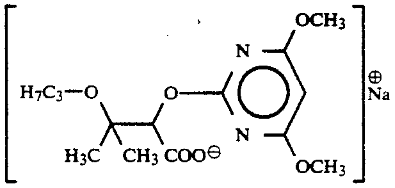 | | | | | | | m.p. 200° C. or higher |

TABLE 1-continued

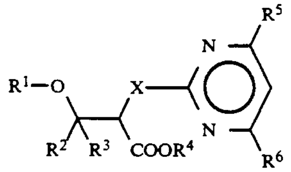

| Compound No. | $R^1$ | $R^2$ | $R^3$ | $R^4$ | $R^5$ | $R^6$ | X | Physical property |
|---|---|---|---|---|---|---|---|---|
| 151 | 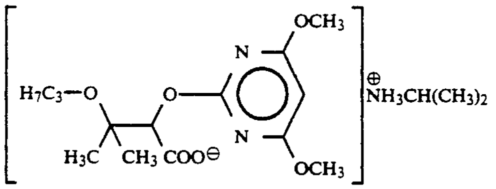 | | | | | | | m.p. 122~124° C. |
| 152 | $CH_3-C\equiv C-CH_2-$ | $CH_3$ | $CH_3$ | $C_2H_5$ | $OCH_3$ | $OCH_3$ | O | m.p. 79~82° C. |
| 153 | " | " | " | H | " | " | " | m.p. 118~121° C. |
| 154 | $C_2H_5$ | " | " | $C_2H_5$ | F | " | " | $n_D^{20.0}$ 1.4814 |
| 155 | $C_2H_5$ | $CH_3$ | $CH_3$ | H | F | $OCH_3$ | " | $n_D^{20.0}$ 1.4816 |
| 156 | $CH_3$ | " | " | " | $OCH_3$ | " | S | m.p. 97~99° C. |
| 157 | $C_2H_5$ | " | " | " | $CH_3$ | $CH_3$ | " | m.p. 106~108° C. |
| 158 | n-$C_3H_7$ | " | " | " | $OCH_3$ | $OCH_3$ | " | m.p. 88~89° C. |
| 159 | $ClCH_2CH_2-$ | " | " | $C_2H_5$ | " | " | O | $n_D^{22.2}$ 1.4902 |
| 160 | " | " | " | H | " | " | " | $n_D^{21.8}$ 1.4840 |
| 161 | " | " | " | " | " | " | S | m.p. 102~103° C. |
| 162 | $ClCH_2CH(CH_3)-$ | H | " | $C_2H_5$ | " | " | O | $n_D^{23.7}$ 1.4895 |
| 163 | $ClCH_2CH(CH_3)-$ | H | $CH_3$ | H | $OCH_3$ | $OCH_3$ | O | m.p. 98~101° C. |
| 164 | " | $CH_3$ | " | $C_2H_5$ | " | " | " | $n_D^{23.0}$ 1.4888 |
| 165 | " | " | " | H | " | " | " | $n_D^{23.0}$ 1.4920 |
| 166 | $BrCH_2CH_2-$ | " | " | $C_2H_5$ | " | " | " | m.p. 60~63° C. |
| 167 | " | " | " | H | " | " | " | Oily product |
| 168 | $(CF_3)_2CH-$ | H | " | $C_2H_5$ | " | " | " | $n_D^{24.2}$ 1.4780 |
| 169 | $HC\equiv C-CH_2-$ | " | " | H | " | " | S | $n_D^{26.6}$ 1.5218 |
| 170 | $CNCH_2CH_2-$ | $CH_3$ | $CH_3$ | $C_2H_5$ | " | " | O | $n_D^{20.0}$ 1.4912 |
| 171 | $CNCH_2CH_2-$ | $CH_3$ | $CH_3$ | H | $OCH_3$ | $OCH_3$ | O | m.p. 110~112° C. |
| 172 | " | " | " | " | " | " | S | m.p. 116~117° C. |
| 173 | i-$C_3H_7-$ | " | " | " | " | " | " | m.p. 97~98° C. |
| 174 | $CF_2HCH_2-$ | " | " | $C_2H_5$ | " | " | O | $n_D^{24.0}$ 1.4601 |
| 175 | " | " | " | H | " | " | " | $n_D^{25.1}$ 1.4819 |
| 176 | " | " | " | " | " | " | S | $n_D^{24.5}$ 1.4968 |

EXAMPLE 2

(1) Preparation of Granule 8 parts by weight of Compound 21 was uniformly mixed with 30 parts by weight of bentonite, 59 parts by weight of talc, 1 part by weight of Neopelex powder (trade name, produced by Kao K.K.) and 2 parts by weight of sodium lignosulfonate, and then the mixture was kneaded with addition of a small amount of water, followed by granulation and drying, to obtain a granule.

(2) Preparation of Wettable Powder 50 parts by weight of Compound 52 was uniformly mixed with 46 parts by weight of kaolin, 2 parts by weight of Neopelex powder (trade name, produced by Kao K.K.) and 2 parts by weight of Demol N (trade name, produced by Kao K.K.), and then the mixture was pulverized to obtain a wettable powder.

(3) Preparation of Emulsion 30 parts by weight of Compound 111 was added to 60 parts by weight of xylene, 5 parts by weight of dimethylformamide and 5 parts by weight of Sorpol 3005X (trade name, produced by Toho Kagaku Kogyo) and uniformly mixed to be dissolved therein to obtain an emulsion.

(4) Preparation of Dust 5 parts by weight of Compound 120 was uniformly mixed with 50 parts by weight of talc and 45 parts by weight of clay to obtain a dust.

EXAMPLE 3

(1) Herbicidal Test for Paddy Field

Wagner pots, each having an area of 1/5000 are, were packed with Ube soil (alluvial soil) and planted with seeds or tubers of barnyardgrass, arrowhead, bulrush and flatstage. Then, the pots were filled with water to a depth of 3 cm.

Each wettable powder of the desired compounds (I) shown in Table 1 prepared in accordance with Example 2 was diluted with water and subjected to dropwise addition treatment by using pipet so that an effective concentration of the compound (I) in each herbicide became 20 g/are at 1 leaf stage of barnyardgrass. These plants were controlled in a glass house at an average temperature of 25° C. for 3 weeks, and then herbicidal effects thereof were investigated.

The herbicidal effects are evaluated according to the 6 ranks (0: None (normal development), 1: Less damaged, 2: Slightly damaged, 3: Moderately damaged, 4: Severely damaged and 5: All killed) as compared with non-treated district.

As a comparative compound, Compound A (Compound No. 76 disclosed in Japanese Provisional Patent Publication No. 85262/1990) shown below was used.

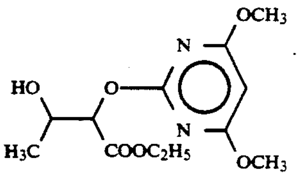

(A)

The results are shown in Table 2.

TABLE 2

| | Kind of weed | | | |
|---|---|---|---|---|
| Compound | Barnyard-grass | Flatstage | Arrowhead | Bulrush |
| 21 | 5 | 5 | 5 | 5 |
| 52 | 5 | 5 | 5 | 5 |
| 111 | 5 | 5 | 5 | 5 |
| A | 0 | 0 | 0 | 0 |

(2) Soil Treatment Test for Upland Field

Wagner pots, each having an area of 1/5000 are, were packed with Ube soil (alluvial soil), and then each seed of cotton, crabgrass, barnyardgrass, common lambsquarter, livid amaranthus and morning glory were planted and covered with soil.

Each wettable powder of the desired compounds (I) shown in Table 1 prepared in accordance with Example 2 was diluted with water and uniformly sprayed on the surface of each soil so that an effective concentration of the compound (I) in each herbicide became 20 g/are. These plants were controlled in a glass house at an average temperature of 25° C. for 3 weeks, and then herbicidal effects thereof were investigated. The herbicidal effects were evaluated according to the evaluation method described in Test example (1), and the results are shown in Table 3 (as a comparative compound, Compound A shown above was used).

TABLE 3

| | Kind of weed | | | | | |
|---|---|---|---|---|---|---|
| Compound | Crabgrass | Barnyardgrass | Common lambsquarter | Livid amaranthus | Morning glory | Cotton |
| 1 | 4 | 4 | 5 | 5 | 2 | 0 |
| 3 | 3 | 4 | 5 | 5 | 3 | 0 |
| 21 | 5 | 5 | 5 | 5 | 4 | 1 |
| 33 | 4 | 5 | 5 | 5 | 3 | 0 |
| 52 | 5 | 5 | 5 | 5 | 5 | 2 |
| 106 | 4 | 3 | 5 | 5 | 4 | 1 |
| 107 | 4 | 3 | 5 | 5 | 3 | 1 |
| 111 | 5 | 5 | 5 | 5 | 4 | 1 |
| 119 | 4 | 4 | 5 | 5 | 3 | 0 |
| 120 | 4 | 4 | 5 | 5 | 4 | 0 |
| A | 2 | 2 | 1 | 1 | 0 | 0 |

(3) Foliar Spread Test for Upland Field

Wagner pots, each having an area of 1/5000 are, were packed with volcanic ash soil and then each seed of crabgrass, barnyardgrass, common lambsquarter, livid amaranthus and morning glory was planted, covered with soil and grown for 2 weeks.

Each wettable powder of the desired compounds (I) shown in Table 1 prepared in accordance with Example 2 was diluted to 2000 ppm with water containing a surfactant (0.05%) and then uniformly sprayed on the above respective plants. After these plants were controlled in a glass house at an average temperature of 25° C. for 3 weeks, the herbicidal effects thereof were investigated. The herbicidal effects were evaluated according to the evaluation method described in Test example (1), and the results are shown in Table 4 (as a comparative compound, Compound A shown above was used).

TABLE 4

| | Kind of weed | | | | |
|---|---|---|---|---|---|
| Compound | Crabgrass | Barnyardgrass | Common lambsquarter | Livid amaranthus | Morning glory |
| 3 | 4 | 5 | 5 | 5 | 4 |
| 5 | 5 | 5 | 5 | 5 | 4 |
| 15 | 3 | 4 | 5 | 5 | 3 |
| 21 | 5 | 5 | 5 | 5 | 4 |
| 33 | 4 | 5 | 5 | 5 | 3 |
| 34 | 5 | 5 | 5 | 5 | 4 |
| 35 | 5 | 5 | 5 | 5 | 5 |
| 52 | 5 | 5 | 5 | 5 | 5 |
| 54 | 5 | 5 | 5 | 5 | 5 |
| 106 | 5 | 5 | 5 | 5 | 4 |
| 107 | 5 | 5 | 5 | 5 | 5 |
| 109 | 5 | 5 | 5 | 5 | 3 |
| 111 | 5 | 5 | 5 | 5 | 5 |
| 113 | 5 | 5 | 5 | 5 | 5 |
| 119 | 4 | 5 | 5 | 5 | 4 |
| 120 | 5 | 5 | 5 | 5 | 5 |
| 122 | 5 | 5 | 5 | 5 | 5 |
| 153 | 4 | 4 | 4 | 5 | 3 |
| 155 | 5 | 5 | 5 | 5 | 5 |
| 156 | 5 | 5 | 5 | 5 | 5 |
| 157 | 5 | 4 | 5 | 5 | 3 |
| 158 | 5 | 5 | 5 | 5 | 5 |
| 160 | 5 | 5 | 5 | 5 | 5 |
| 161 | 5 | 5 | 5 | 5 | 5 |
| 163 | 5 | 5 | 5 | 5 | 3 |
| 165 | 5 | 5 | 5 | 5 | 5 |
| 166 | 3 | 5 | 5 | 5 | 3 |
| 167 | 5 | 5 | 5 | 5 | 5 |
| 168 | 5 | 5 | 5 | 5 | 5 |
| 169 | 5 | 5 | 5 | 5 | 5 |
| 170 | 5 | 5 | 5 | 5 | 5 |
| 171 | 5 | 5 | 5 | 5 | 5 |
| 172 | 5 | 5 | 5 | 5 | 5 |

TABLE 4-continued

| | Kind of weed | | | | |
|---|---|---|---|---|---|
| Compound | Crabgrass | Barnyardgrass | Common lambsquarter | Livid amaranthus | Morning glory |
| A | 2 | 3 | 1 | 1 | 1 |

The novel 3-alkoxyalkanoic acid derivative of the present invention has high selectivity to annual and perennial weeds, and also shows excellent herbicidal effect (particularly effective on annual grass weeds and broad-leaved weeds).

We claim:

1. A 3-alkoxyalkanoic acid compound represented by the following formula (I):

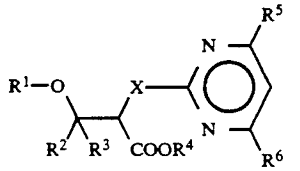

(I)

wherein $R^1$ is an alkyl group having 1 to 6 carbon atoms which may be substituted by a cycloalkyl group having 3 to 8 carbon atoms, an alkenyl group having 2 to 6 carbon atoms, an alkynyl group having 2 to 6 carbon atoms, a cycloalkyl group having 3 to 8 carbon atoms, a haloalkyl group having 2 to 6 carbon atoms, or a cyanoalkyl group having 2 to 6 carbon atoms; $R^2$ is a hydrogen atom or an alkyl group having 1 to 5 carbon atoms; $R^3$ is an alkyl group having 1 to 6 carbon atoms; or $R^2$ and $R^3$ may be mutually bonded to form a cycloalkyl group having 3 to 8 carbon atoms; $R^4$ is a hydrogen atom, an alkyl group having 1 to 5 carbon atoms or an alkynyl group having 2 to 5 carbon atoms; $R^5$ is an alkoxy group having 1 to 5 carbon atoms or an alkyl group having 1 to 5 carbon atoms; $R^6$ is an alkoxy group having 1 to 5 carbon atoms, an alkyl group having 1 to 5 carbon atoms or a halogen atom; and X is an oxygen atom or a sulfur atom, or an alkali addition salt thereof.

2. The 3-alkoxyalkanoic acid compound according to claim 1, wherein $R^1$ is an alkyl group having 1 to 4 carbon atoms, a straight or branched alkyl group having 1 to 3 carbon atoms which may be substituted by a cycloalkyl group having 3 to 5 carbon atoms, a straight or branched alkenyl group having 2 to 5 carbon atoms, a straight or branched alkynyl group having 2 to 5 carbon atoms, a cycloalkyl group having 3 to 6 carbon atoms, a haloalkyl group having 2 to 4 carbon atoms or a straight or branched cyanoalkyl group having 2 to 4 carbon atoms.

3. The 3-alkoxyalkanoic acid compound according to claim 1, wherein $R^1$ is methyl group, ethyl group, n-propyl group, i-propyl group, n-butyl group, i-butyl group, sec-butyl group, t-butyl group, cyclopropylmethyl group, cyclobutylmethyl group, propenyl group, propynyl group or cyclohexyl group.

4. The 3-alkoxyalkanoic acid compound according to claim 1, wherein said compound is at least one selected from the group consisting of:

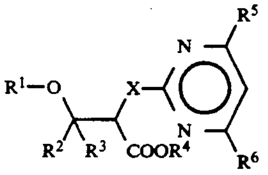

| Compound No. | $R^1$ | $R^2$ | $R^3$ | $R^4$ | $R^5$ | $R^6$ | X | Physical property |
|---|---|---|---|---|---|---|---|---|
| 1 | $CH_3$ | H | $CH_3$ | $CH_3$ | $OCH_3$ | $OCH_3$ | O | m.p. 83~85° C. |
| 2 | " | " | " | $C_2H_5$ | " | " | " | |
| 3 | " | " | " | H | " | " | " | m.p. 127~129° C. |
| 4 | " | " | " | $C_2H_5$ | " | " | S | |
| 5 | " | " | " | H | " | " | " | m.p. 84~86° C. |
| 6 | " | " | " | $C_2H_5$ | $CH_3$ | " | O | |
| 7 | " | " | " | H | " | " | " | |
| 8 | " | " | " | $C_2H_5$ | " | $CH_3$ | " | |
| 9 | $CH_3$ | H | $CH_3$ | H | $CH_3$ | $CH_3$ | O | |
| 10 | " | " | " | $C_2H_5$ | Cl | $OCH_3$ | " | |
| 11 | " | " | " | H | " | " | " | |
| 12 | " | " | " | $C_2H_5$ | $CF_3$ | " | " | |
| 13 | " | " | " | H | " | " | " | |
| 14 | " | " | $C_2H_5$ | $C_2H_5$ | $OCH_3$ | " | " | |
| 15 | " | " | " | H | " | " | " | |
| 16 | " | " | n-$C_3H_7$ | $CH_3$ | " | " | " | $n_D^{24.8}$ 1.4520 |
| 17 | $CH_3$ | H | n-$C_3H_7$ | H | $OCH_3$ | $OCH_3$ | O | m.p. 92~94° C. |
| 18 | " | " | i-$C_3H_7$ | $CH_3$ | " | " | " | $n_D^{28.4}$ 1.4868 |
| 19 | " | " | " | H | " | " | " | |
| 20 | " | $CH_3$ | $CH_3$ | $C_2H_5$ | " | " | " | m.p. 89~91° C. |
| 21 | " | " | " | H | " | " | " | m.p. 143~145° C. |
| 22 | " | " | " | i-$C_3H_7$ | " | " | " | m.p. 73~75° C. |
| 23 | " | " | $C_2H_5$ | $C_2H_5$ | " | " | " | m.p. 70~71° C. |
| 24 | " | " | " | H | " | " | " | m.p. 138~140° C. |
| 25 | $CH_3$ | $CH_3$ | 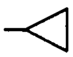 | $C_2H_5$ | $OCH_3$ | $OCH_3$ | O | |
| 26 | " | " | " | H | " | " | " | |

-continued

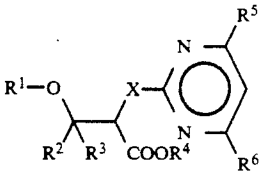

| Compound No. | $R^1$ | $R^2$ | $R^3$ | $R^4$ | $R^5$ | $R^6$ | X | Physical property |
|---|---|---|---|---|---|---|---|---|
| 27 | " | $C_2H_5$ | $C_2H_5$ | $C_2H_5$ | " | " | " | m.p. 66~67° C. |
| 28 | " | " | " | H | " | " | " | m.p. 163~165° C. |
| 29 | " | 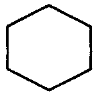 | | $C_2H_5$ | " | " | " | m.p. 109~110° C. |
| 30 | " | | " | H | " | " | " | m.p. 131~133° C. |
| 31 | $C_2H_5$ | H | $CH_3$ | $CH_3$ | " | " | " | Oily product |
| 32 | " | " | " | $C_2H_5$ | " | " | " | m.p. 56~58° C. |
| 33 | $C_2H_5$ | H | $CH_3$ | H | $OCH_3$ | $OCH_3$ | O | m.p. 111~113° C. |
| 34 | " | " | " | $C_2H_5$ | " | " | S | Oily product |
| 35 | " | " | " | H | " | " | " | $n_D^{24.6}$ 1.5238 |
| 36 | " | " | " | $C_2H_5$ | $CH_3$ | " | O | |
| 37 | " | " | " | H | " | " | " | |
| 38 | " | " | " | $C_2H_5$ | " | $CH_3$ | " | |
| 39 | " | " | " | H | " | " | " | |
| 40 | " | " | " | $C_2H_5$ | Cl | $OCH_3$ | O | |
| 41 | $C_2H_5$ | H | $CH_3$ | H | Cl | $OCH_3$ | O | |
| 42 | " | " | " | $C_2H_5$ | $CF_3$ | " | " | |
| 43 | " | " | " | H | " | " | " | |
| 44 | " | " | $C_2H_5$ | $C_2H_5$ | $OCH_3$ | " | " | $n_D^{23.8}$ 1.4704 |
| 45 | " | " | " | H | " | " | " | m.p. 121~123° C. |
| 46 | " | " | n-$C_3H_7$ | $C_2H_5$ | " | " | " | $n_D^{24.8}$ 1.4798 |
| 47 | " | " | " | H | " | " | " | m.p. 123~125° C. |
| 48 | " | " | i-$C_3H_7$ | $C_2H_5$ | " | " | " | $n_D^{26.8}$ 1.4628 |
| 49 | $C_2H_5$ | H | i-$C_3H_7$ | H | $OCH_3$ | $OCH_3$ | O | m.p. 115~117° C. |
| 50 | " | $CH_3$ | $CH_3$ | $C_2H_5$ | " | " | " | m.p. 81~83° C. |
| 51 | " | " | " | t-$C_4H_9$ | " | " | " | |
| 52 | " | " | " | H | " | " | " | m.p. 121~122° C. |
| 53 | " | " | " | $C_2H_5$ | " | " | S | Oily product |
| 54 | " | " | " | H | " | " | " | m.p. 96~98° C. |
| 55 | " | " | " | $C_2H_5$ | $CH_3$ | " | O | $n_D^{23.0}$ 1.4812 |
| 56 | " | " | " | H | " | " | " | m.p. 130~132° C. |
| 57 | $C_2H_5$ | $CH_3$ | $CH_3$ | $C_2H_5$ | $CH_3$ | $CH_3$ | O | |
| 58 | " | " | " | H | " | " | " | |
| 59 | " | " | " | $C_2H_5$ | Cl | $OCH_3$ | " | $n_D^{26.6}$ 1.4858 |
| 60 | " | " | " | H | " | " | " | |
| 61 | " | " | " | $C_2H_5$ | $CF_3$ | " | " | $n_D^{25.0}$ 1.4470 |
| 62 | " | " | " | H | " | " | " | m.p. 73~75° C. |
| 63 | " | " | $C_2H_5$ | $C_2H_5$ | $OCH_3$ | " | " | m.p. 47~48° C. |
| 64 | " | " | " | H | " | " | " | m.p. 83~85° C. |
| 65 | $C_2H_5$ | $CH_3$ | 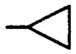 | $C_2H_5$ | $OCH_3$ | $OCH_3$ | O | |
| 66 | " | " | " | H | " | " | " | |
| 67 | " | $C_2H_5$ | $C_2H_5$ | $C_2H_5$ | " | " | " | $n_D^{26.4}$ 1.4815 |
| 68 | " | " | " | H | " | " | " | m.p. 131~133° C. |
| 69 | " | 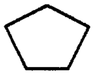 | | $C_2H_5$ | " | " | " | m.p. 82~83° C. |
| 70 | " | | " | H | " | " | " | m.p. 156~158° C. |
| 71 | " | 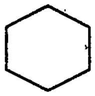 | | $C_2H_5$ | " | " | " | m.p. 89~91° C. |
| 72 | " | | " | H | " | " | " | m.p. 173~175° C. |
| 73 | n-$C_3H_7$ | H | $CH_3$ | $C_2H_5$ | $OCH_3$ | $OCH_3$ | O | $n_D^{26.2}$ 1.4776 |
| 74 | " | " | " | n-$C_3H_7$ | " | " | " | $n_D^{26.6}$ 1.4764 |
| 75 | " | " | " | H | " | " | " | $n_D^{25.6}$ 1.4866 |
| 76 | " | " | n-$C_3H_7$ | $C_2H_5$ | " | " | " | $n_D^{28.5}$ 1.4799 |
| 77 | " | " | " | H | " | " | " | m.p. 129~131° C. |

-continued

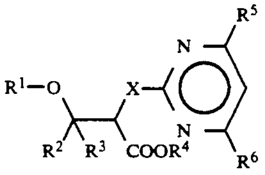

| Compound No. | $R^1$ | $R^2$ | $R^3$ | $R^4$ | $R^5$ | $R^6$ | X | Physical property |
|---|---|---|---|---|---|---|---|---|
| 78 | " | " | i-$C_3H_7$ | n-$C_3H_7$ | " | " | " | $n_D^{27.8}$ 1.4718 |
| 79 | " | $CH_3$ | $CH_3$ | $C_2H_5$ | " | " | " | m.p. 51~53° C. |
| 80 | " | " | " | t-$C_4H_9$ | " | " | " | m.p. 66~68° C. |
| 81 | n-$C_3H_7$ | $CH_3$ | $CH_3$ | $C_2H_5$ | $CF_3$ | $OCH_3$ | O | $n_D^{24.5}$ 1.4480 |
| 82 | " | " | " | H | " | " | " | m.p. 78~80° C. |
| 83 | " | " | " | " | $OCH_3$ | " | " | m.p. 99~101° C. |
| 84 | i-$C_3H_7$ | H | " | $C_2H_5$ | " | " | " | $n_D^{24.0}$ 1.4732 |
| 85 | " | " | " | i-$C_3H_7$ | " | " | " | m.p. 87~89° C. |
| 86 | " | " | " | t-$C_4H_9$ | " | " | " | |
| 87 | " | " | " | H | " | " | " | m.p. 106~108° C. |
| 88 | " | " | " | $C_2H_5$ | " | " | S | $n_D^{27.8}$ 1.5050 |
| 89 | i-$C_3H_7$ | H | $CH_3$ | $C_2H_5$ | $CH_3$ | $OCH_3$ | O | $n_D^{23.3}$ 1.4727 |
| 90 | " | " | " | H | " | " | " | m.p. 117~120° C. |
| 91 | " | " | " | $C_2H_5$ | " | $CH_3$ | " | |
| 92 | " | " | " | H | " | " | " | |
| 93 | " | " | " | $C_2H_5$ | Cl | $OCH_3$ | " | $n_D^{25.0}$ 1.4918 |
| 94 | " | " | " | H | " | " | " | Yellowish oily product |
| 95 | " | " | " | $C_2H_5$ | $CF_3$ | " | " | |
| 96 | " | " | " | H | " | " | " | |
| 97 | i-$C_3H_7$ | H | $C_2H_5$ | $C_2H_5$ | $OCH_3$ | $OCH_3$ | O | $n_D^{25.2}$ 1.4675 |
| 98 | " | " | n-$C_3H_7$ | " | " | " | " | $n_D^{26.8}$ 1.4742 |
| 99 | " | " | " | H | " | " | " | m.p. 129-131° C. |
| 100 | " | " | i-$C_3H_7$ | $C_2H_5$ | " | " | " | $n_D^{26.8}$ 1.4688 |
| 101 | " | " | " | i-$C_3H_7$ | " | " | " | $n_D^{26.8}$ 1.4508 |
| 102 | " | " | " | H | " | " | " | Oily product |
| 103 | " | $CH_3$ | $CH_3$ | $C_2H_5$ | " | " | " | m.p. 64~66° C. |
| 104 | " | " | " | H | " | " | " | Measurement impossible |
| 105 | i-$C_3H_5$ | 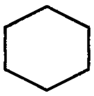 | | $C_2H_5$ | $OCH_3$ | $OCH_3$ | O | $n_D^{27.8}$ 1.4909 |
| 106 | $CH_2{=}CH{-}CH_2{-}$ | H | $CH_3$ | " | " | " | " | $n_D^{25.0}$ 1.4879 |
| 107 | " | " | " | H | " | " | " | m.p. 84~86° C. |
| 108 | " | " | " | $C_2H_5$ | " | " | S | |
| 109 | " | " | " | H | " | " | " | $n_D^{23.6}$ 1.5277 |
| 110 | " | $CH_3$ | " | $C_2H_5$ | " | " | O | m.p. 63~64° C. |
| 111 | " | " | " | H | " | " | " | m.p. 65~67° C. |
| 112 | " | " | " | $C_2H_5$ | " | " | S | |
| 113 | $CH_2{=}CH{-}CH_2{-}$ | $CH_3$ | $CH_3$ | H | $OCH_3$ | $OCH_3$ | S | m.p. 83~84° C. |
| 114 | " | 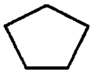 | | $C_2H_5$ | " | " | O | m.p. 53~55° C. |
| 115 | " | " | | H | " | " | " | m.p. 94~95° C. |
| 116 | $HC{\equiv}C{-}CH_2{-}$ | H | $CH_3$ | $C_2H_5$ | " | " | " | $n_D^{27.0}$ 1.4911 |
| 117 | " | " | " | H | " | " | " | $n_D^{24.6}$ 1.5104 |
| 118 | " | $CH_3$ | " | $C_2H_5$ | " | " | " | $n_D^{28.4}$ 1.4960 |
| 119 | " | " | " | $-CH_2C{\equiv}CH$ | " | " | " | $n_D^{28.4}$ 1.5020 |
| 120 | " | " | " | H | " | " | " | m.p. 136~137° C. |
| 121 | $HC{\equiv}C{-}CH_2{-}$ | $CH_3$ | $CH_3$ | $C_2H_5$ | $OCH_3$ | $OCH_3$ | S | |
| 122 | " | " | " | H | " | " | " | m.p. 81~83° C. |
| 123 | n-$C_4H_9$ | H | " | $C_2H_5$ | " | " | O | m.p. 66~68° C. |
| 124 | " | " | " | n-$C_4H_9$ | " | " | " | $n_D^{24.0}$ 1.4750 |
| 125 | " | $CH_3$ | " | $C_2H_5$ | " | " | " | m.p. 53~55° C. |
| 126 | " | " | " | H | " | " | " | m.p. 103~104° C. |
| 127 | sec-$C_4H_9$ | H | " | $C_2H_5$ | " | " | " | Measurement impossible |
| 128 | " | " | " | sec-$C_4H_9$ | " | " | " | $n_D^{25.0}$ 1.4738 |
| 129 | sec-$C_4H_9$ | $CH_3$ | $CH_3$ | $C_2H_5$ | $OCH_3$ | $OCH_3$ | O | |
| 130 | " | " | " | H | " | " | " | |
| 131 | i-$C_4H_9$ | H | " | $C_2H_5$ | " | " | " | |
| 132 | " | " | " | H | " | " | " | |
| 133 | " | $CH_3$ | " | $C_2H_5$ | " | " | " | |
| 134 | " | " | " | H | " | " | " | |
| 135 | 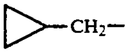 | H | " | $C_2H_5$ | " | " | " | $n_D^{23.6}$ 1.4921 |

-continued

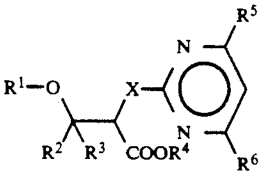

| Compound No. | $R^1$ | $R^2$ | $R^3$ | $R^4$ | $R^5$ | $R^6$ | X | Physical property |
|---|---|---|---|---|---|---|---|---|
| 136 | " | " | " | H | " | " | " | |
| 137 | 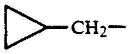 | $CH_3$ | $CH_3$ | $C_2H_5$ | $OCH_3$ | $OCH_3$ | O | m.p. 85~87° C. |
| 138 | " | " | " | H | " | " | " | m.p. 105~106° C. |
| 139 | 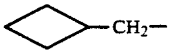 | H | " | $C_2H_5$ | " | " | " | $n_D^{24.8}$ 1.4867 |
| 140 | " | " | " | H | " | " | " | $n_D^{25.0}$ 1.5020 |
| 141 | " | $CH_3$ | " | $C_2H_5$ | " | " | " | m.p. 74~77° C. |
| 142 | " | " | " | H | " | " | " | m.p. 118~119° C. |
| 143 | 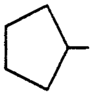 | H | " | $C_2H_5$ | " | " | " | Oily product |
| 144 | $CF_3CH_2$— | " | " | " | " | " | " | $n_D^{26.8}$ 1.4552 |
| 145 | $CF_3CH_2$— | H | $CH_3$ | H | $OCH_3$ | $OCH_3$ | O | |
| 146 | " | $CH_3$ | " | $C_2H_5$ | " | " | " | m.p. 54~56° C. |
| 147 | " | " | " | H | " | " | " | m.p. 128~130° C. |
| 148 | 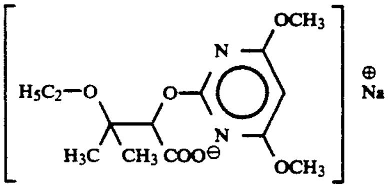 | | | | | | | m.p. 200° C. or higher |
| 149 | 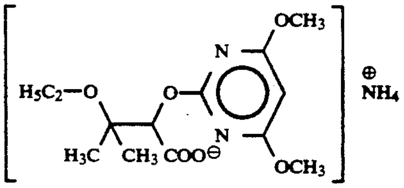 | | | | | | | |
| 150 | 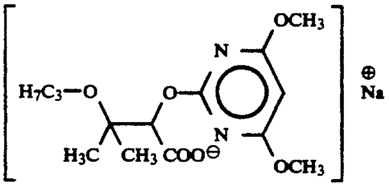 | | | | | | | m.p. 200° C. or higher |
| 151 | 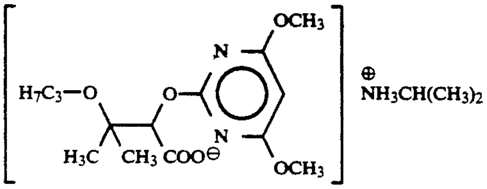 | | | | | | | m.p. 122~124° C. |
| 152 | $CH_3-C{\equiv}C-CH_2-$ | $CH_3$ | $CH_3$ | $C_2H_5$ | $OCH_3$ | $OCH_3$ | O | m.p. 79~82° C. |
| 153 | " | " | " | H | " | " | " | m.p. 118~121° C. |

-continued

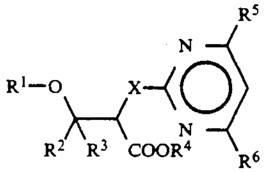

| Compound No. | $R^1$ | $R^2$ | $R^3$ | $R^4$ | $R^5$ | $R^6$ | X | Physical property |
|---|---|---|---|---|---|---|---|---|
| 154 | $C_2H_5$ | " | " | $C_2H_5$ | F | " | " | $n_D^{20.0}$ 1.4814 |
| 155 | $C_2H_5$ | $CH_3$ | $CH_3$ | H | F | $OCH_3$ | " | $n_D^{20.0}$ 1.4816 |
| 156 | $CH_3$ | " | " | " | $OCH_3$ | " | S | m.p. 97~99° C. |
| 157 | $C_2H_5$ | " | " | " | $CH_3$ | $CH_3$ | " | m.p. 106~108° C. |
| 158 | n-$C_3H_7$ | " | " | " | $OCH_3$ | $OCH_3$ | " | m.p. 88~89° C. |
| 159 | $ClCH_2CH_2$— | " | " | $C_2H_5$ | " | " | O | $n_D^{22.2}$ 1.4902 |
| 160 | " | " | " | H | " | " | " | $n_D^{21.8}$ 1.4840 |
| 161 | " | " | " | " | " | " | S | m.p. 102~103° C. |
| 162 | $ClCH_2CH(CH_3)$— | H | " | $C_2H_5$ | " | " | O | $n_D^{23.7}$ 1.4895 |
| 163 | $ClCH_2CH(CH_3)$— | H | $CH_3$ | H | $OCH_3$ | $OCH_3$ | O | m.p. 98~101° C. |
| 164 | " | $CH_3$ | " | $C_2H_5$ | " | " | " | $n_D^{23.0}$ 1.4888 |
| 165 | " | " | " | H | " | " | " | $n_D^{23.0}$ 1.4920 |
| 166 | $BrCH_2CH_2$— | " | " | $C_2H_5$ | " | " | " | m.p. 60~63° C. |
| 167 | " | " | " | H | " | " | " | Oily product |
| 168 | $(CF_3)_2CH$— | H | " | $C_2H_5$ | " | " | " | $n_D^{24.2}$ 1.4780 |
| 169 | HC≡C—$CH_2$— | " | " | H | " | " | S | $n_D^{26.6}$ 1.5218 |
| 170 | $CNCH_2CH_2$— | $CH_3$ | $CH_3$ | $C_2H_5$ | " | " | O | $n_D^{20.0}$ 1.4912 |
| 171 | $CNCH_2CH_2$— | $CH_3$ | $CH_3$ | H | $OCH_3$ | $OCH_3$ | O | m.p. 110~112° C. |
| 172 | " | " | " | " | " | " | S | m.p. 116~117° C. |
| 173 | i-$C_3H_7$— | " | " | " | " | " | " | m.p. 97~98° C. |
| 174 | $CF_2HCH_2$— | " | " | $C_2H_5$ | " | " | O | $n_D^{24.0}$ 1.4601 |
| 175 | " | " | " | H | " | " | " | $n_D^{25.1}$ 1.4819 |
| 176 | " | " | " | " | " | " | S | $n_D^{24.5}$ 1.4968 |

5. The 3-alkoxyalkanoic acid compound according to claim 4, wherein said compound is at least one selected from the compounds identified in claim 4 as Compound Nos. 1, 2, 6, 8, 10, 12, 14, 16, 18, 20, 22, 23, 25, 27, 29, 31, 32, 36, 38, 40, 42, 44, 46, 48, 50, 51, 55, 57, 59, 61, 63, 65, 67, 69, 71, 73, 74, 76, 78, 79, 80, 81, 84, 85, 86, 89, 91, 93, 95, 97, 98, 100, 101, 103, 105, 106, 110, 114, 116, 118, 119, 123, 124, 125, 127, 128, 129, 131, 133, 135, 137, 139, 141, 143, 144, 146, 152, 154, 159, 162, 164, 166, 168, 170 and 174.

6. The 3-alkoxyalkanoic acid compound according to claim 4, wherein said compound is at least one selected from the compounds identified in claim 4 as Compound Nos. 4, 5, 34, 35, 53, 54, 88, 108, 109, 112, 113, 121, 122, 156, 157, 158, 161, 169, 172, 173 and 176.

7. The 3-alkoxyalkanoic acid compound according to claim 4, wherein said compound is at least one selected from the compounds identified in claim 4 as Compound Nos. 1, 3, 6-13, 31, 33, 36-43, 50, 52, 55-62, 73, 74, 75, 81, 82, 84, 85, 87, 89-96, 106, 107, 110, 111, 116-120, 123, 124, 127, 128, 131, 132, 135-147, 152, 153, 159, 160, 164-168, 170, 171, 174 and 175.

8. The 3-alkoxyalkanoic acid compound according to claim 4, wherein said compound is at least one selected from the compounds identified in claim 4 as Compound Nos. 1, 3, 6-13, 31, 33, 36-43, 55-62, 73, 74, 75, 81, 82, 84, 85, 87, 89-96, 106, 107, 110, 111, 116-120, 123, 124, 127, 128, 131, 132, 135-147, 152, 153, 159, 160, 162-168, 170, 171, 174 and 175.

9. The 3-alkoxyalkanoic acid compound according to claim 7, wherein said compound is identified in claim 4 as Compound No. 154 or 155.

10. A herbicide comprising a 3-alkoxyalkanoic acid compound represented by the following formula (I):

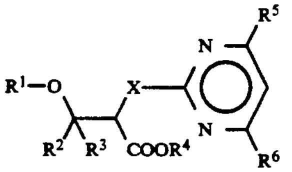

(I)

wherein $R^1$ is an alkyl group having 1 to 6 carbon atoms which may be substituted by a cycloalkyl group having 3 to 8 carbon atoms, an alkenyl group having 2 to 6 carbon atoms, an alkynyl group having 2 to 6 carbon atoms, a cycloalkyl group having 3 to 8 carbon atoms, a haloalkyl group having 2 to 6 carbon atoms, or a cyanoalkyl group having 2 to 6 carbon atoms; $R^2$ is a hydrogen atom or an alkyl group having 1 to 5 carbon atoms; $R^3$ is an alkyl group having 1 to 6 carbon atoms; or $R^2$ and $R^3$ may be mutually bonded to form a cycloalkyl group having 3 to 8 carbon atoms; $R^4$ is a hydrogen atom, an alkyl group having 1 to 5 carbon atoms or an alkynyl group having 2 to 5 carbon atoms; $R^5$ is an alkoxy group having 1 to 5 carbon atoms or an alkyl group having 1 to 5 carbon atoms; $R^6$ is an alkoxy group having 1 to 5 carbon atoms, an alkyl group having 1 to 5 carbon atoms or a halogen atom; and X is an oxygen atom or a sulfur atom, or an alkali addition salt thereof as an active ingredient and a herbicidally effective carrier.

* * * * *

UNITED STATES PATENT AND TRADEMARK OFFICE

CERTIFICATE OF CORRECTION

PATENT NO. : 5,178,663

DATED : January 12, 1993

INVENTOR(S) : Katsumasa Harada

It is certified that error appears in the above-indentified patent and that said Letters Patent is hereby corrected as shown below:

Claim 7, column 31, line 63, change "164-168" to -- 162-168--.

Signed and Sealed this

Eleventh Day of January, 1994

Attest:

Bruce Lehman

BRUCE LEHMAN

Attesting Officer

*Commissioner of Patents and Trademarks*